United States Patent [19]   [11]  4,323,518
Gilligan   [45]  Apr. 6, 1982

[54] POLYNITROETHYLTHIONOCARBONATES AND METHOD OF PREPARATION

[75] Inventor: William H. Gilligan, Fort Washington, Md.

[73] Assignee: The United States of America as represented by the Secretary of the Navy, Washington, D.C.

[21] Appl. No.: 235,305

[22] Filed: Feb. 17, 1981

[51] Int. Cl.$^3$ ............................................. C07C 154/00
[52] U.S. Cl. .................................................. 260/455 B
[58] Field of Search ..................................... 260/455 B

[56] References Cited

U.S. PATENT DOCUMENTS 3,694,482  9/1972  Engelhart ......................... 260/455 B Primary Examiner—Henry R. Jiles
Assistant Examiner—Robert C. Whittenbaugh
Attorney, Agent, or Firm—R. S. Sciascia; A. L. Branning; R. D. Johnson

[57]   ABSTRACT

Bis(2,2-dinitropropyl)thionocarbonate, $[CH_3C(NO_2)_2CH_2O]_2C=S$; bis(2,2,2-trinitroethyl)thionocarbonate, $[C(NO_2)_3CH_2O]_2C=S$; and bis(2,2-difluoro-2-nitroethyl)thionocarbonate, $[CF_2(NO_2)CH_2O]_2C=S$ are prepared by reacting one mole of 1,1'-thiocarbonyldi-1,2,4-triazole with 2 moles of 2,2-dinitropropanol, 2,2,2-trinitroethanol, or 2,2-difluoro-2-nitroethanol, respectively. These compounds are useful as explosives and as intermediates for the preparation of energetic explosives and plasticizers.

5 Claims, No Drawings

POLYNITROETHYLTHIONOCARBONATES AND METHOD OF PREPARATION

BACKGROUND OF THE INVENTION

This invention relates to nitroorganic compounds and more particularly to nitroalkylthionocarbonates.

U.S. Pat. No. 4,172,088 which was issued to Angres et al in October, 1979 discloses the preparation of bis(2-fluoro-2,2-dinitroethyl)thionocarbonate by the reaction of fluorodinitroethanol with thiophosgene under basic conditions.

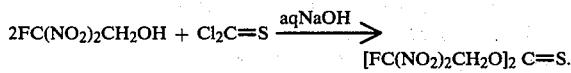

$$2FC(NO_2)_2CH_2OH + Cl_2C=S \xrightarrow{aqNaOH} [FC(NO_2)_2CH_2O]_2 C=S.$$

This method works well with 2-fluorosubstituted alcohols, but with alcohols substituted only with nitro groups in the 2-position, deformylation of the alcohol

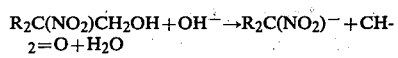

$$R_2C(NO_2)CH_2OH + OH^- \rightarrow R_2C(NO_2)^- + CH_2=O + H_2O$$

occurs preferentially to thionocarbonate formation. Thus this method is unsuitable for the preparation of thionocarbonates of trinitroethanol and dinitropropanol. The method is also unsuitable for difluoronitroethanol but in this case it is due to extensive hydrolysis of the initially formed thionocarbonate to the carbonate.

SUMMARY OF THE INVENTION

Accordingly, an object of this invention is to provide novel organic compounds.

Another object of this invention is to provide novel energetic explosives.

A further object of this invention is to provide a method.

These and other objects of this invention are achieved by providing the following compounds $[CH_3C(NO_2)_2CH_2O]_2 C=S$,
$[C(NO_2)_3CH_2O]_2 C=S$, and
$[CF_2(NO_2)CH_2O]_2 C=S$, which are prepared by reacting 1 mole of 1,1'-thiocarbonyldi-1,2,4-triazole with two moles of $CH_3C(NO_2)_2CH_2OH$, $C(NO_2)_3CH_2OH$; or $CF_2(NO_2)CH_2OH$, respectively.

These compounds are useful as explosives and as intermediates for the preparation of energetic explosives and plasticizers.

DETAILED DESCRIPTION OF THE INVENTION

Recent investigations in organo-sulfur chemistry have utilized, in particular, 1,1-thiocarbonyldiimidazole and 1,1'-thiocarbonyldi-1,2,4-triazole as thiocarbonyl transfer reagents for the preparation of thionocarbonates and thioureas. 1,1'-Thiocarbonyl diimidazole was ineffective due to side reactions involving the nitroalcohol and imidazole. However when 1,1'-thiocarbonyl-di-1,2,4-triazole was reacted with 2,2-dinitropropanol and 2,2-difluoro-2-nitroethanol good yields of the respective thionocarbonates were obtained under mild basic conditions. With trinitroethanol under the same conditions again side-reactions predominated with copious gassing and destruction of the trinitroethanol. The compound, bis(trinitroethyl)thionocarbonate, was finally obtained by adding trifluoroacetic acid to the reaction medium to tie up 1,2,4-triazole as it was liberated, thereby allowing the reaction to proceed under acidic conditions. Generally in acylation reactions of this type trinitroethanol will not react under acidic conditions, however in this case, protonation of the triazole moiety of the thio-carbonyl transfer reagent probably occurs thereby increasing the reactivity sufficiently for reaction to occur.

The reactions of nitroalcohols and fluoroalcohols with 1,1'-thiocarbonyldi-1,2,4-triazole can be carried out in chlorinated hydrocarbon solvents or acetone at ice bath (0°) to room temperature (25° C.) with or without catalytic amounts of pyridine as a catalyst. For trinitroethanol, the addition of trifluoroacetic acid or an other organic acid such as acetic or, propionic is essential for success.

This is the only method available for the preparation of bis(2,2-dinitropropyl)thionocarbonate, bis(3,3,3-trinitroethyl)thionocarbonate, and bis(2,2-difluoro-2-nitroethyl)thionocarbonate. While these compounds are explosives and energetic additives in their own right, they are particularly valuable as intermediates for the preparation of polynitroethyl dichloroformals, 2:2 "mixed" polynitroethylorthocarbonates, polynitroethyl difluoroformals and polynitroethylorthocarbonate prepolymers and polymers.

To more clearly illustrate this invention, the following examples are presented. It should be understood, however, that these examples are presented merely as a means of illustration and are not intended to limit the scope of the invention in any way.

EXAMPLE 1

Bis(2,2-dinitropropyl)thionocarbonate

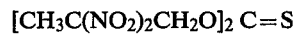

$[CH_3C(NO_2)_2CH_2O]_2 C=S$

To a solution of 4.50 g (0.03 mol) of 2,2-dinitropropanol in 50 ml of acetone was added 4.90 g (0.027 mol) of 1,1'-thiocarbonyldi-1,2,4-triazole and 0.5 ml of pyridine. After standing at ambient temperature for two days, the acetone was removed on a rotavac and the solid residue thoroughly washed with water. After air drying, the crude product was recrystallized from chloroform to give 4.27 g (83%) of product, mp 86°–7°. H-NMR (CDCl$_3$/TMS) δS(ppm)-S, 5.21, 2H; s, 2.22, 3H. Calc. for $C_7H_{10}N_4O_{10}S$. C, 24.56; H, 2.95; N, 16.37; S, 9.37. Found C, 24.54; H, 2.96; N, 16.09, S, 9.08.

EXAMPLE 2

Bis(3,3,3-trinitroethyl)thionocarbonate

$[C(NO_2)_3CH_2O]_2 C=S$

A methylene chloride solution (100 ml), containing 5.07 g (28 mmol) of trinitroethanol, 3.20 g (28 mmol) of trifluoroacetic acid and 2.50 g (14 mmol) of 1,1'-thiocarbonyldi-1,2,4-triazole, was stirred at ambient temperature for 14 days. The solution was then washed with three 100 ml portions of water, dried with magnesium sulfate, filtered and the volatiles removed on a rotavoc. The residual oil was washed several times with water by decantation until the oil solidified. The crude product, after drying, was chromatographed on silica gel and eluted with methylene chloride/hexane (1/1) to give in the initial eluates 1.1 g (20%) of a white crystalline product, m.p. 92°–3°.

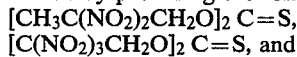

H-NMR (CD Cl$_3$/TMS) δS(ppm)-s, 5.74. Calc. for C$_5$H$_4$N$_6$O$_{14}$S. C, 14.86; H, 1.00; S, 7.93. Found. C, 15.11; H, 1.02; S, 7.54

EXAMPLE 3

Bis(2,2-fluoro-2-nitroethyl)thionocarbonate

[CF$_2$(NO$_2$)CH$_2$O]$_2$ C=S

To a solution of 5.59 g (44.0 mmol) of 2,2-difluoro-2-nitroethanol and 3.60 g (20.0 mmol) of 1,1'-thiocarbonyldi-1,2,4-triazole in 50 ml of dry methylene chloride was added 0.5 ml pyridine. The solution, after stirring for two hours, was washed with five 100 ml portions of water. After drying with magnesium sulfate and filtering, the volatiles were removed in vacuo the residue was distilled through a short path apparatus to give 4.2 g (71%) of product, b.p. about 63°/0.1 torr.

H-NMR (CDCl$_3$/TMS) δS(ppm)-t, 5.15. Calc. for C$_5$H$_4$N$_2$O$_6$S. C, 20.28; H, 1.36; F, 25.66; N, 9.46; S, 10.83. Found. C, 20.56; H, 1.37; F, 25.89; N, 9.19; S, 10.63.

Although dry methylene chloride was used as the solvent for the reactions in these examples, other inert chlorohydrocarbon solvents, such as chloroform, 1,2-dichloroethane, and 1,1,2-trichloroethane, may also be used.

The reactions are carried out in a temperature range of from 0° C. to 25° C. (ambient room temperature). It is preferable to mix the reactants together at the lower end of this temperature range to prevent overheating and then complete the reaction at ambient room temperature.

Obviously, many modifications and variations of the present invention are possible in light of the above teachings. It is therefore to be understood that within the scope of the appended claims the invention may be practiced otherwise than as specifically described.

What is claimed as new and desired to be secured by Letters Patent of the United States is:

1. Bis(2,2-dinitropropyl)thionocarbonate.
2. Bis(2,2,2-trinitroethyl)thionocarbonate.
3. Bis(2,2-difluoro-2-nitroethyl)thiocarbonate.
4. A method of preparing a compound selected from the group consisting of bis(2,2-dinitropropyl)thionocarbonate, bis(2,2-difluoro-2-nitroethyl)thionocarbonate, and bis(2,2,2-trinitroethyl)thionocarbonate by reacting an appropriate alcohol selected from the group consisting of 2,2-dinitropropanol, 2,2-difluoro-2-nitroethanol, and 2,2,2-trinitroethanol with 1,1'-thiocarbonyldi-1,2,4-triazole in the presence of pyridine at a temperature in the range of from 0° C. to 25° C., provided that when bis(2,2,2-trinitroethyl)thionocarbonate is being prepared a strong organic acid is added.
5. The method of claim 4 wherein the strong organic acid is trifluoroacetic acid.

* * * * *